United States Patent [19]

Waite

[11] 3,950,515

[45] *Apr. 13, 1976

[54] ANIMAL FEEDS CONTAINING ANTIBIOTIC AV290

[75] Inventor: Jack Peter Waite, Fareham, England

[73] Assignee: American Cyanamid Company, Stamford, Conn.

[ * ] Notice: The portion of the term of this patent subsequent to Dec. 24, 1991, has been disclaimed.

[22] Filed: Sept. 5, 1974

[21] Appl. No.: 503,557

Related U.S. Application Data

[62] Division of Ser. No. 355,240, April 27, 1973, Pat. No. 3,856,937.

[52] U.S. Cl................................ 424/115; 424/123
[51] Int. Cl.².......................................... A61K 35/00
[58] Field of Search..................... 424/118, 123, 115

[56] References Cited
UNITED STATES PATENTS

| | | | |
|---|---|---|---|
| 3,338,786 | 8/1967 | Kunstmann | 424/118 |
| 3,832,462 | 8/1974 | Shu et al. | 424/118 |
| 3,856,937 | 12/1974 | Waite | 424/115 |

*Primary Examiner*—Frederick E. Waddell
*Attorney, Agent, or Firm*—Edward A. Conroy, Jr.

[57] ABSTRACT

This disclosure describes a reversible complex of antibiotic AV290 with an alkali metal alkyl sulfate and a process for preparing same. The complex is useful as an animal feed supplement which significantly enhances the growth rate of animals and poultry.

7 Claims, No Drawings

ANIMAL FEEDS CONTAINING ANTIBIOTIC AV290

CROSS REFERENCE TO RELATED APPLICATION

This application is a division of my copending application Ser. No. 355,240, filed Apr. 27, 1973 now U.S. Pat. No. 3,856,937.

BRIEF SUMMARY OF THE INVENTION

This invention relates to a method of recovering antibiotic AV290 from fermentation whole harvest mashes containing it. More particularly, the process involves adding an alkali metal alkyl sulfate (or mixtures thereof) either to the whole harvest mash or to the filtered fermentation liquor, and recovering the so precipitated antibiotic-alkyl sulfate reversible complex (or mixture of complexes) by any convenient means. The invention also relates to the use of the so prepared complex in animal feed supplement compositions for enhancing the growth rate of animals such as poultry, swine, early weaned pigs, and ruminants such as cattle, sheep and goats.

DETAILED DESCRIPTION OF THE INVENTION

Antibiotic AV290 is formed by fermentative biosynthesis during the cultivation under controlled conditions of *Streptomyces candidus* NRRL 3218 and mutants thereof. The preparation and properties of antibiotic AV290 are set forth in U.S. Pat. No. 3,338,786 which is hereby incorporated by reference. The problem of recovering the antibiotic economically has been a serious one. In the patent referred to above, adsorption on charcoal followed by elution and column chromatography are employed. Such a process is not excessively expensive when pure antibiotic is required for medical usage. However, when the antibiotic is to be used in animal feed supplement compositions the factor of cost is a very serious matter and there is, therefore, a need for an inexpensive process of recovering the antibiotic for this purpose.

The present invention deals with a process and in a more specific aspect also with a product. The process involves the precipitation of the antibiotic either from the whole harvest mash or from the filtered fermentation broth by the addition of alkali metal alkyl sulfates. The alkali metal alkyl sulfates operable in the novel process of the present invention may be represented by the following general formula:

$$CH_3-(CH_2)_n-O-SO_2-OM$$

wherein $n$ is an integer from 9 to 17, inclusive, and $M$ is sodium or potassium. Typical such alkali metal alkyl sulfates which may be employed are, for example, sodium decyl sulfate, potassium hendecyl sulfate, sodium lauryl sulfate, potassium tridecyl sulfate, sodium myristyl sulfate, potassium pentadecyl sulfate, sodium cetyl sulfate, potassium heptadecyl sulfate, and sodium octadecyl sulfate. Mixtures of alkali metal alkyl sulfates may also be employed such as a mixture of sodium hendecyl sulfate and potassium octadecyl sulfate; a mixture of potassium decyl sulfate and sodium heptadecyl sulfate; a mixture of potassium lauryl sulfate and potassium cetyl sulfate; a mixture of sodium tridecyl sulfate, potassium myristyl sulfate, and sodium pentadecyl sulfate; and the like. When mixtures of alkali metal alkyl sulfates are employed, then a corresponding mixture of antibiotic-alkyl sulfate complexes are obtained.

The novel process of the present invention provides almost complete removal of the antibiotic activity from the fermentation mash or broth. Furthermore, the antibiotic-alkyl sulfate complex so obtained can be used without separation of the constituents in animal feed supplement compositions, which is an important economic advantage. Therefore, in one of the aspects of the present invention the complex of antibiotic AV290 and an alkali metal alkyl sulfate is included as a product.

The product of the antibiotic and alkali metal alkyl sulfate has been referred to as a reversible antibiotic-alkyl sulfate complex. Its exact chemical nature has not been determined, but covalent bonding is not involved and the product is not a physical mixture. This complex, derived from the interaction of the antibiotic and an alkali metal alkyl sulfate, is not necessarily combined in any limiting stoichiometry. The chemical bonds are reversible since the antibiotic AV290 may be recovered from the complex by various means such as adsorption on a cross-linked carboxymethyldextran gel column followed by elution with aqueous acid. While it is not intended to limit the present invention to theories of chemical constitution and the like, it seems probable that the complex of the present invention is sufficiently reversible so that under conditions of use in animal feed supplement compositions the antibiotic is set free upon ingestion.

As starting material for the novel process of the present invention there may be employed the whole harvest mash obtained after completion of a fermentation with *S. candidus* NRRL 3218 or mutants thereof. Preferably, there is employed the fermentation liquor or broth which has been clarified by removing the mycelia and other insolubles by filtration. Diatomaceous earth or any other conventional filtration aid may be used to assist in the filtration. In either case, the pH of the whole mash or of the filtered broth is first adjusted to between 1.9 and 2.1, preferably about 2.0, with an acid. Suitable acids for this purpose may be, for example, hydrochloric acid, sulfuric acid, trifluoroacetic acid, and the like, although even glacial acetic acid may be used. This pH adjustment appears to be critical since below pH 1.9 there appears to be degradation of antibiotic AV290 during drying of the filter cake even at 40°C. under vacuum. Then, an aqueous solution of an alkali metal alkyl sulfate (or a mixture of alkali metal alkyl sulfates) is added slowly, with stirring, at ambient temperatures. The entire process of the present invention is preferably carried out at from about 15°C. to about 30°C., conveniently at room temperature. The antibiotic and alkyl sulfate form a complex which is water insoluble and thus precipitates. The precipitated complex or, in the case of the whole mash, the precipitated complex together with the fermentation mash solids, is then removed by filtration or centrifugation and dried. The products so obtained may be dried by (1) slurrying the wet solids in polar, water miscible non-solvents such as acetone followed by filtration, rinsing and air-drying; or by (2) reslurrying the wet solids in water and freeze drying or spray drying.

When the products of the present invention are thus carefully dried under temperature conditions which do not degrade antibiotic AV290, they are usually white to tan powders in the case of the alkyl sulfate complex. In the case of the alkyl sulfate complex associated with dried harvest mash solids, they are usually gray to brown powders or solids. In the dry form, these products are extremely stable, keeping without significant loss of antibiotic activity for considerable periods of time. This long storage life is, of course, an important practical advantage.

It is an advantage of the present invention that the amount of alkali metal alkyl sulfate added to precipitate the complex with the antibiotic is not particularly critical and no exact stoichiometric relations need be followed. In general, the amount of alkali metal alkyl sulfate required to precipitate antibiotic AV290 from a whole harvest mash is 1.5-2.5 grams per gram of AV290 activity in the mash. In the usual case, about 2.0 grams of alkali metal alkyl sulfate per gram of antibiotic activity in the mash is preferred. The AV290 content of the whole mash may be readily determined by microbiological assay (after adjusting the pH to 8.0-9.0) as set forth in U.S. Pat. No. 3,338,786. The preferred method is an adaptation of the *Staphylococcus aureus* turbidimetric assay for tetracycline that is described in "Assay Methods of Antibiotics, a Laboratory Manual" by Grove & Randall, Medical Encyclopedia, Inc. (1955), pages 48-52. The required amount of alkali metal alkyl sulfate is then preferably dissolved or suspended in a convenient quantity of water and the aqueous solution or suspension is added to the whole mash as described above. Any excess alkali metal alkyl sulfate present will merely remain in solution upon filtration.

In general, the amount of alkali metal alkyl sulfate required to precipitate antibiotic AV290 from a clarified liquor is about one gram per gram of AV290 activity in the clarified liquor. The higher level of alkali metal alkyl sulfate required to precipitate AV290 from whole mash than from clarified liquor is due to coprecipitation of other protein material present in the whole mash. Conveniently, the minimum amount of alkali metal alkyl sulfate required to form the complex with the antibiotic in the clarified liquor from any particular fermentation batch may be readily determined as follows. A sample (conveniently 50-100 ml.) of the fermentation whole harvest mash is taken and clarified by removing the mycelia and other insolubles by filtration, preferably with a filter aid. The filtrate is then acidified to a pH of 1.9-2.1 with dilute aqueous mineral acid such as dilute hydrochloric acid, dilute sulfuric acid, dilute phosphoric acid, or the like. This solution is then titrated with the particular aqueous solution of alkali metal alkyl sulfate which is to be used until no further precipitate or turbidity forms. The amount of alkali metal alkyl sulfate solution for the clarified liquor of the fermentation batch is then calculated from the titer of the sample taken, providing also for a slight excess.

This invention also relates to animal feed supplement compositions effective in accelerating the growth rate of animals and poultry. In recent years the use of antibiotics in animal feeds for improving growth characteristics and efficiency of feed utilization has become of considerable economic importance. In accordance with the present invention, the dried alkyl sulfate complex or the dried harvest mash solids containing the alkyl sulfate complex, either alone or in combination with suitable carriers, when added to an animal feed, aid in increasing the growth rate. In addition, feed efficiency is improved. The present invention has the advantage that the growth rate of non-ruminants such as poultry and swine and especially weanling pigs is significantly increased, and that feed conversion rates are noticeably enhanced.

The feed supplement compositions of the present invention are administered in an amount sufficient to furnish approximately the following dosage levels in mg./head/day:

| Large ruminants | 350 |
| Small ruminants | 200 |
| Non-ruminants | 100 |
| Poultry | 2 |

The milligrams per pound of antibiotic AV290 present in any particular supplement composition of the present invention may be readily determined by bioassay (after adjusting the pH to 8.0-9.0) as set forth in U.S. Pat. No. 3,338,786. The preferred method is an adaptation of the *Staphylococcus aureus* turbidimetric assay for tetracycline that is described in the manual "Assay Methods of Antibiotics, a Laboratory Manual" by D. C. Grove and W. A. Randall, Medical Encyclopedia Inc. (1955) pages 48-52. From the potency data thus obtained, the pounds of feed supplement composition to be used per ton of feed may be readily calculated.

A wide variety of carriers may be used in the preparation of the feed supplement compositions of this invention containing the dried alkyl sulfate complex or the dried harvest mash solids containing the alkyl sulfate complex. Carriers suitable for use to make up the feed supplement compositions include the following: soybean meal, alfalfa meal, cotton seed oil meal, linseed oil meal, cornmeal, cane molasses, urea, bone meal, corncob meal, and the like. The carrier promotes a uniform distribution of the complex in the finished feed into which the supplement is blended. It thus performs an important function by ensuring proper distribution of the complex throughout the feed.

For a clearer understanding of the invention, specific examples of it are set forth below. These examples are merely illustrative, and are not to be understood as limiting the scope and underlying principles of the invention in any way.

EXAMPLE 1

Precipitation of Antibiotic AV290-Sodium Lauryl Sulfate Complex from Clarified Liquor For these tests, a sample of technical AV290 sulfate having a microbiological potency of 63.8% was employed. Portions of the AV290 sulfate were dissolved in water and the pH of the solutions were adjusted to 2.0 with 15% $H_2SO_4$. Celite 545 (a diatomaceous earth) was added as a filter aid and 2% aqueous sodium lauryl sulfate solution was added dropwise with stirring. The slurry was aged for 30 minutes at room temperature and the solids were removed by filtration and dried under vacuum at 40°C. The spent filtrate and dry solids were assayed microbiologically and the results are set forth in Table I below.

TABLE I

| Test No. | AV290 conc. g./liter | Ratio $C_{12}H_{25}OSO_3Na$:AV290 | Spent filtrate | % of input in dry cake | AV290 Balance |
|---|---|---|---|---|---|
| 1 | 9.57 | 0.785 | 0.9 | 84.9 | 85.8 |
| 2 | 6.38 | 0.785 | 1.5 | 93.5 | 95.0 |
| 3 | 3.19 | 0.785 | 2.8 | 89.9 | 92.7 |

EXAMPLE 2

Precipitation of Antibiotic AV290-Sodium Lauryl Sulfate Complex from Whole Harvest Mash Samples of S. candidus shaker flask fermentation whole harvest mashes were taken and the potency thereof "boosted" by the addition of technical AV290 sulfate. In the tests tabulated in Table II below, 100 ml. portions of mash were employed and the pH thereof was adjusted to 2.0 with 15% aqueous sulfuric acid. Then, 3.0 grams of Dicalite 478 (a diatomaceous earth) were added and 2% aqueous sodium lauryl sulfate solution was added dropwise with stirring. The slurrys were aged for three hours at room temperature and the solids were removed by filtration and dried under vacuum at 40°C. The spent filtrates and dry cakes were assayed microbiologically and the results are set forth in Table II below.

TABLE II

| Test No. | 1 | 2 | 3 | 4 | 5 | 6 | 7 | 8 |
|---|---|---|---|---|---|---|---|---|
| Mash assay in γ/ml. | 1300 | 1300 | 1400 | 1400 | 1130 | 1130 | 975 | 975 |
| Mash boosted to Γ/ml. | 5130 | 5130 | 5230 | 5230 | 4960 | 4960 | — | — |
| Ratio of $C_{12}H_{25}OSO_3Na$:AV290 | 0.78 | 0.78 | 1.15 | 1.53 | 1.61 | 2.02 | 3.08 | 4.10 |
| % of input in- spent filtrate | 44.8 | 48.5 | 20.3 | 12.0 | 12.0 | 6.5 | 9.2 | 6.2 |
| dry cake | 49.9 | 50.7 | 76.7 | 85.6 | 87.6 | 90.5 | 88.6 | 88.7 |
| AV290 balance | 94.7 | 99.2 | 97.0 | 97.6 | 99.6 | 97.0 | 97.8 | 94.9 |

EXAMPLE 3

Effect of pH on Precipitation of the Complex from Whole Harvest Mash

Samples of S. candidus fermentation whole harvest mashes were "boosted" to 4,930 γ/ml. by the addition of technical AV290 sulfate and the pH of the samples were adjusted with 15% aqueous sulfuric acid as tabulated in Table III below. Then, 3.0 grams of Dicalite 478 were added followed by 40 ml. of a 2% aqueous sodium lauryl sulfate solution, added dropwise with stirring, to a $C_{12}H_{25}OSO_3Na$:AV290 ratio of 1.62. The slurrys were aged for three hours at room temperature and the solids were removed by filtration and dried under vacuum at 40°C. The spent filtrates and dry cakes were assayed microbiologically and the results are set forth in Table III below.

TABLE III

| Sample No. | 1 | 2 | 3 | 4 | 5 |
|---|---|---|---|---|---|
| pH of mash for precipitation | 1.6 | 1.8 | 2.0 | 2.2 | 2.4 |
| % of input in- spent filtrate | 7.3 | 6.4 | 6.1 | 6.9 | 10.1 |
| dry cake | 55.3 | 71.6 | 92.8 | 83.3 | 64.2 |
| AV290 balance | 62.6 | 78.0 | 98.9 | 90.2 | 74.3 |

EXAMPLE 4

Precipitation of Antibiotic AV290 from Whole Harvest Mash Using Sodium Lauryl Sulfate A 30 liter sample of pilot fermenter mash having a microbiological assay of 3,740 γ/ml. was treated as follows. The pH of the mash was adjusted to 2.0 by the addition of 219 ml. of concentrated sulfuric acid, and then one kg. of Dicalite 478 was added as a filter aid. To the stirred mash was slowly added a solution of 240 gm. of sodium lauryl sulfate in 3 liters of water. The treated mash was then aged with stirring for one hour at room temperature and the solids were removed by means of a filter press. The filter cake was dried under vacuum at 50°C. whereby there was obtained 1,978 gm. of dry product having a microbiological assay of 4.72%. This represents an antibiotic AV290 recovery from mash to dry cake of 83.2%.

EXAMPLE 5

Precipitation of Antibiotic AV290 from Whole Harvest Mash using Sodium Decyl Sulfate A 400 ml. sample of whole shaker flask mash (microbiological assay 4,590 γ/ml.) was adjusted to pH 2.0 by the addition of 3.9 ml. of concentrated sulfuric acid, and then 5 grams of Dicalite 478 were added as a filter aid. To the stirred mash were slowly added 9.68 grams of Empicol 0137 (a 30.5% active solution of sodium decyl sulfate manufactured by Albright & Wilson Chemicals, Ltd.) diluted to 50 ml. with water. The treated mash was then aged with stirring for one hour at room temperature and the solids were removed by means of a vacuum filter. The filter cake was dried under vacuum at 50°C. whereby there was obtained 20.2 grams of dry product having a microbiological assay of 9.14%. This represents an antibiotic AV290 recovery from mash to dry cake of 100.5%.

EXAMPLE 6

Precipitation of Antibiotic AV290 from Whole Harvest Mash Using a Mixture of Sodium Cetyl Sulfate and Sodium Oleyl Sulfate A 400 ml. sample of whole shaker flask mash (microbiological assy 4,590 γ/ml.) was adjusted to pH 2.0 by the addition of 3.9 ml. of concentrated sulfuric acid, and then 5 grams of Dicalite 478 were added as a filter aid. To the stirred mash were slowly added 13.51 grams of Empicol CHC 30 (a 30% active paste of a mixture of sodium cetyl sulfate and sodium oleyl sulfate manufactured by Albright & Chemicals, Ltd.) dispersed in water to give a total dispersion volume of 50 ml. The treated mash was then aged with stirring for one hour at room temperature and the solids were removed by means of a vacuum filter. The filter cake was dried under vacuum at 50°C. whereby there was obtained 24.0 grams of dry product having a microbiological assay of 8.08%. This represents an antibiotic AV290 recovery from mash to dry cake of 105.6%.

EXAMPLE 7

Growth Promoting Effect of Antibiotic AV290-lauryl Sulfate Complex

Experimental Design

The evaluation of a growth promoter is based on average results obtained with a series of four 2-week feeding tests. In each test, there are three pens of ten chicks for each treatment.

Test Materials

AV290-lauryl sulfate complex was tested at levels of 5, 10, 20 and 40 ppm. of AV290 equivalent in the diet.

Diet

The basal diet used in these experiments was Broiler Ration No. 453 (Table V). Experimental diets were prepared by mixing the appropriate amount of test material with the basal diet in a Hobart Mixer. All diets were fed ad libitum and feeding of experimental diets was begun upon arrival of the chicks.

Brooding

Day-old Hubbard × Arbor Acres broiler chicks were housed in electrically heated brooders in an air-conditioned room (24°C.) for 2 weeks. There were five male and five female chicks per pen.

Data

Data recorded included initial weights, average sexed weights at 2 weeks, and 2-week feed consumption.

Results

AV290-lauryl sulfate complex improved weight gain and feed utilization at all levels tested. The degree of response was related to the amount of antibiotic fed. Average 2-week results from all four tests are as follows in Table IV with percent improvement over control in brackets.

TABLE IV

| Treatment | Level[a] (ppm) | Average Gain/Chick(g) | Feed/Gain Ratio |
|---|---|---|---|
| Control | — | 191.38 | 1.46 |
| AV290-lauryl sulfate complex | 5 | 200.12 (4.6) | 1.43 (2.4) |
| AV290-lauryl sulfate complex | 10 | 200.12 (4.8) | 1.42 (2.6) |
| AV290-lauryl sulfate complex | 20 | 204.65 (6.9) | 1.40 (4.6) |
| AV290-lauryl sulfate complex | 40 | 212.08 (10.8) | 1.38 (5.8) |

[a] As AV290 equivalent

TABLE V

| BROILER RATION NO. 453 | |
|---|---|
| Ingredient | % |
| Ground yellow corn | 53.45 |
| Soybean oil meal (49%) | 28.0 |
| Menhaden fish meal (60%) | 5.0 |
| Corn gluten meal (60%) | 5.0 |
| Dehydrated alfalfa meal (17%) | 2.0 |
| Stabilized fat | 4.0 |
| Dicalcium phosphate | 1.2 |

TABLE V-continued

| BROILER RATION NO. 453 | |
|---|---|
| Ingredient | % |
| Ground Limestone | 0.5 |
| Sodium chloride | 0.3 |
| *Tra-Min No. 3 | 0.05 |
| **Vitamin premix | 0.5 |
| Total | 100.00 |

| **Vitamin Premix for 1-Ton | |
|---|---|
| Ingredient | grams |
| DL methionine | 453.6 |
| BHT | 113.6 |
| Vitaamin A (30,000 μ/g) | 100.0 |
| Vitamin D₃ (200,000 μ/g) | 5.0 |
| Vitamin E (20,000 μ/lb) | 45.4 |
| Riboflavin | 4.0 |
| Niacinamide | 25.0 |
| Ca. Pantothenate | 8.0 |
| Vitamin K (menadione) | 1.0 |
| Parvo (10%), folic acid | 13.0 |
| Choline Chloride (50%) | 908.0 |
| Proferm (20 mg B₁₂/lb) | 227.0 |
| Corn Oil | 50.0 |
| Fine ground corn | 2582.4 |
| Total | 4536.0 |

| *Tra-Min No. 3 | | |
|---|---|---|
| Element | % | 1 lb/Ton Furnishes (ppm) |
| Manganese | 12.50 | 62.5 |
| Iron | 6.00 | 30.0 |
| Zinc | 5.00 | 25.0 |
| Copper | 0.65 | 3.25 |
| Iodine | 0.35 | 1.75 |
| Cobalt | 0.25 | 1.25 |
| Calcium min. | 15.30 | |
| max. | 18.35 | |

I claim:

1. A process for the production of a dried fermentation harvest mash solids animal feed supplement containing an antibiotic AV290-alkyl sulfate complex which comprises the steps of:
   a. acidifying a fermentation whole harvest mash containing antibiotic AV290 to a pH of from 1.9 to 2.1 with a pharmacologically acceptable acid;
   b. adding to the acidified mash a complexing agent selected from the group consisting of compounds of the formula:

$$CH_3-(CH_2)_n-O-SO_2-OM$$

wherein $n$ is an integer from 9 to 17, inclusive, and $M$ is sodium or potassium, and mixtures thereof until a sufficient amount of the antibiotic AV290-alkyl sulfate complex is imparted to said medium;
   c. removing the harvest mash solids together with the precipitated antibiotic AV290-alkyl sulfate complex; and
   d. drying the mixture of mash solids and antibiotic AV290-alkyl sulfate complex.

2. A process according to claim 1 wherein the complexing agent is sodium decyl sulfate.

3. A process according to claim 1 wherein the complexing agent is sodium lauryl sulfate.

4. A process according to claim 1 wherein the complexing agent is a mixture of sodium cetyl sulfate and sodium oleyl sulfate.

5. An animal feed supplement of a dry mixture of fermentation harvest mash solids and an effective amount for accelerating the growth rate of animals of antibiotic AV290-alkyl sulfate complex prepared in accordance with the process of claim 1.

6. An animal feed composition which comprises a nutritionally balanced animal feed and an effective amount for accelerating the growth rate of animals of a dry mixture of fermentation harvest mash solids and antibiotic AV290-alkyl sulfate complex prepared in accordance with the process of claim 1.

7. An animal feed composition which comprises a nutritionally balanced animal feed and an effective amount for accelerating the growth rate of animals of a dry antibiotic AV290-alkyl sulfate complex prepared from a fermentation whole harvest mash containing antibiotic AV290 by a process which comprises the steps of:
 a. producing a fermentation liquor by filtering the whole harvest mash;
 b. acidifying the fermentation liquor to a pH of from 1.9 to 2.1 with a pharmacologically acceptable acid;
 c. adding to the acidified liquor a complexing agent selected from the group consisting of compounds of the formula:

$$CH_3\text{-}(CH_2)_n\text{-}O\text{-}SO_2\text{-}OM$$

wherein $n$ is an integer from 9 to 17, inclusive, and M is sodium or potassium, and mixtures thereof until a sufficient amount of the antibiotic AV290-alkyl sulfate complex is imparted to said medium;
 d. removing the precipitated antibiotic AV290-alkyl sulfate complex; and
 e. drying the antibiotic AV290-alkyl sulfate complex.

* * * * *